(12) United States Patent
Kai et al.

(10) Patent No.: US 8,871,520 B2
(45) Date of Patent: Oct. 28, 2014

(54) URACIL-SPECIFIC FLUORESCENCE DETECTION REACTION AND METHOD FOR EXAMINING DIHYDROPYRIMIDINE DEHYDROGENASE DEFICIENCY

(75) Inventors: Masaaki Kai, Nagasaki (JP); Takayuki Shibata, Nagasaki (JP)

(73) Assignee: Nagasaki University, Kagasaki (JP)

( * ) Notice: Subject to any disclaimer, the term of this patent is extended or adjusted under 35 U.S.C. 154(b) by 42 days.

(21) Appl. No.: 13/582,356

(22) PCT Filed: Mar. 1, 2011

(86) PCT No.: PCT/JP2011/054636
§ 371 (c)(1),
(2), (4) Date: Nov. 5, 2012

(87) PCT Pub. No.: WO2011/108544
PCT Pub. Date: Sep. 9, 2011

(65) Prior Publication Data
US 2013/0052678 A1    Feb. 28, 2013

(30) Foreign Application Priority Data

Mar. 1, 2010   (JP) ................. 2010-044610

(51) Int. Cl.
| | | |
|---|---|---|
| *G01N 21/64* | (2006.01) | |
| *G01N 21/00* | (2006.01) | |
| *C07C 251/00* | (2006.01) | |
| *C09K 11/06* | (2006.01) | |
| *G01N 33/533* | (2006.01) | |
| *C12Q 1/32* | (2006.01) | |

(52) U.S. Cl.
CPC ............ *G01N 21/6428* (2013.01); *C09K 11/06* (2013.01); *C09K 2211/1074* (2013.01); *G01N 33/533* (2013.01); *C12Q 1/32* (2013.01); *G01N 2333/90206* (2013.01)
USPC ................... 436/98; 436/96; 436/91; 435/26; 435/25; 544/267; 544/244; 544/1; 564/299; 564/225; 564/1

(58) Field of Classification Search
CPC ... G01N 21/64; G01N 21/21; G01N 21/6428; C12Q 1/68; C12Q 1/6806; C12Q 1/6844
USPC ............. 436/98, 96, 91; 435/26, 25; 544/267, 544/244, 1; 564/229, 225, 1
See application file for complete search history.

(56) References Cited

U.S. PATENT DOCUMENTS

| | | |
|---|---|---|
| 6,927,035 B1 | 8/2005 | Soma |
| 2002/0072080 A1 | 6/2002 | Yoshikubo et al. |

FOREIGN PATENT DOCUMENTS

| | | |
|---|---|---|
| JP | 2001-112472 A | 4/2001 |
| JP | 2008-120824 A | 5/2008 |

OTHER PUBLICATIONS

Harris et al., *Cancer Research*, 50: 197-201 (1990).
Kawasaki et al., *The Japan Society for Analytical Chemistry Dai 57 Nenkai Koen Yoshishu*, 370, Item Y1079 (Aug. 27, 2008).
Mattison et al., *Clinical Cancer Research*, 10: 2652-2658 (2004).
Shibata et al., *Analytica Chimica Acta*, 674(2): 234-238 (2010).
Sumi et al., *Journal of Chromatography B*, 672: 233-239 (1995).
Takaba et al., *The Japanese Journal of Gastroenterological Surgery*, 41(12): 2075-2080 (2008).
International Bureau of WIPO, International Preliminary Report on Patentability in International Patent Application No. PCT/JP2011/054636 (Nov. 7, 2012).
Japanese Patent Office, International Search Report in International Patent Application No. PCT/JP2011/054636 (Apr. 19, 2011).
Kawasaki et al., "The development of a novel fluorescence reaction which can identify a pyrimidine base and the elucidation of the reaction mechanism," poster presentation at *The Japan Society for Analytical Chemistry Nenkai 57* (Sep. 2008).

*Primary Examiner* — Christine T Mui

(74) *Attorney, Agent, or Firm* — Leydig, Voit & Mayer, Ltd.

(57) ABSTRACT

The invention provides a method of detecting uracil. The method comprises reacting uracil with a compound represented by the formula (I) in the presence of an oxidant and a base to produce a fluorescent compound represented by the formula (II).

12 Claims, 5 Drawing Sheets

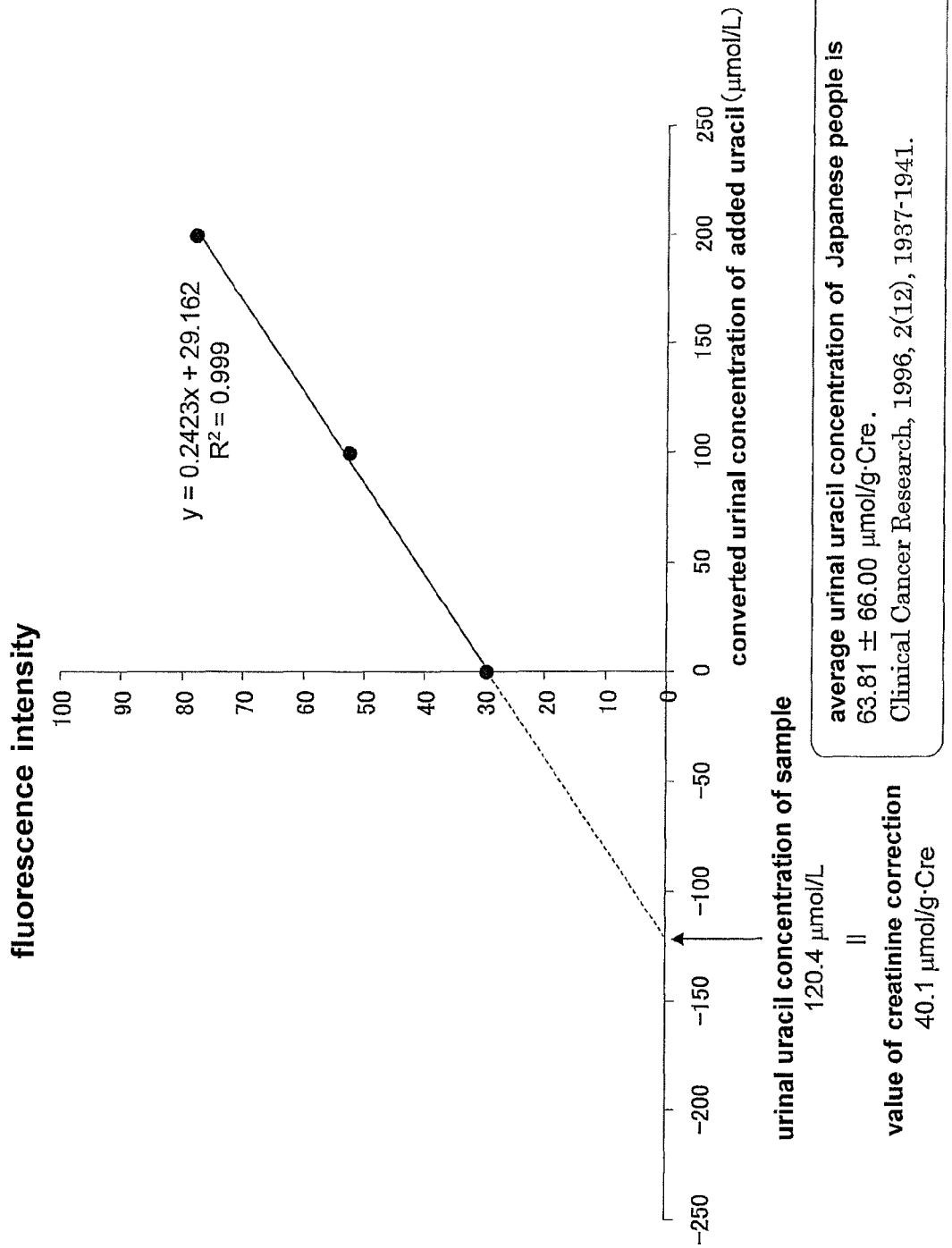

URACIL-SPECIFIC FLUORESCENCE DETECTION REACTION AND METHOD FOR EXAMINING DIHYDROPYRIMIDINE DEHYDROGENASE DEFICIENCY

CROSS-REFERENCE TO RELATED APPLICATIONS

This patent application is the U.S. national phase of International Patent Application PCT/JP2011/054636, filed on Mar. 1, 2011, which claims the benefit of Japanese Patent Application No. 2010-044610, filed on Mar. 1, 2010, which are incorporated by reference in their entireties herein.

TECHNICAL FIELD

The present invention relates to a method of detecting uracil-specific fluorescence, a reagent for uracil detection, and a method for examining dihydropyrimidine dehydrogenase deficiency by using the reaction.

BACKGROUND ART

Fluorinated pyrimidine anti-cancer agents including 5-fluorouracil (5-FU) are representative anti-cancer agents frequently used for malignant tumors such as breast cancer, gastrointestinal cancer and the like. It is known, however, that administration of a fluorinated pyrimidine anti-cancer agent to a patient genetically defective in dihydropyrimidine dehydrogenase (DPD), which is a rate-determining enzyme in fluorinated pyrimidine decomposition, raises blood concentration of fluorinated pyrimidine, as well as causes serious side effects such as blood disorder, bone marrow suppression and the like, which could lead to death in the worst case. Since DPD is an enzyme that generally degrades uracil and thymine, DPD-defective patients are known to show high concentrations of uracil and thymine, particularly uracil, in urine or blood. Therefore, quantification of the concentration of uracil in urine or blood of patients before administration of a fluorinated pyrimidine anti-cancer agent to the patients enables diagnosis of DPD deficiency, based on which an accident due to the administration of a fluorinated pyrimidine anti-cancer agent to DPD defective patients can be prevented.

As a method of quantifying uracil in urine or blood, a method using high performance liquid chromatography (HPLC) (S. Sumi, K. Kidouchi, S. Ohba and Y. Wada, J. Chromatogr. B 1995, 672, 233-239), and an immunological measurement method using an anti-uracil monoclonal antibody (JP-A-2008-120824 and JP-A-2001-112472) have heretofore been developed. However, the HPLC method is associated with defects in that measurement of one sample takes time and multiple samples cannot be analyzed simultaneously, an expensive apparatus is necessary and the like. The immunological measurement method is also associated with defects in that substrate specificity is low and determination of DPD deficiency is difficult, it is costly and the like.

As a DPD activity measurement method other than quantification of uracil, a method of directly measuring the DPD activity of peripheral blood mononuclear cells (B. E. Harris, R. Song, S. Soong and R. B. Diasio, Cancer Res. 1990, 50, 197-201), and a method including administering uracil labeled with a radioisotope and measuring the content of metabolized labeled $CO_2$ in the breath (L. K. Mattison, H. Ezzeldin, M. Carpenter, A. Modak, M. R. Johnson and R. B. Diasio, Clin. Cancer Res., 2004, 10, 2652-2658) have been reported. However, they are associated with various problems in that the former does not permit simultaneous analysis of multiple samples since it requires HPLC separation, and the latter uses radioactive substances, may misdiagnose as DPD deficiency due to the influence of other enzymes and the like.

With such background, the DPD activity measurement methods developed heretofore are not used for routine examination in hospitals, and at present, the DPD activity of patient is measured only when a side effect such as nausea and the like or abnormality in blood examination is observed after administration of a fluorinated pyrimidine anti-cancer agent. Therefore, many cases of death have been reported in the world, which were caused by aggravation of side effects even though administration of fluorinated pyrimidine was discontinued after finding DPD deficiency (Tomoyuki Takaba, Jin Moriyama, Tsuyoshi Yokoyama, Shuichiro Matoba, Toshihito Sawada, The Japanese Journal of Gastroenterological Surgery, 2008, vol. 41, pages 2075-2080).

Therefore, the development of a uracil quantification method and a DPD deficiency examination method, which are capable of detecting uracil highly accurately and economically by a convenient method in a short time, has been desired.

DOCUMENT LIST

Patent Documents

Patent document 1: JP-A-2008-120824
Patent document 2: JP-A-2001-112472

Non-Patent Documents

Non-patent document 1: S. Sumi, K. Kidouchi, S. Ohba and Y. Wada, J. Chromatogr. B 1995, 672, 233-239
Non-patent document 2: B. E. Harris, R. Song, S. Soong and R. B. Diasio, Cancer Res. 1990, 50, 197-201
Non-patent document 3: L. K. Mattison, H. Ezzeldin, M. Carpenter, A. Modak, M. R. Johnson and R. B. Diasio, Clin. Cancer Res., 2004, 10, 2652-2658
Non-patent document 4: Tomoyuki Takaba, Jin Moriyama, Tsuyoshi Yokoyama, Shuichiro Matoba, Toshihito Sawada, The Japanese Journal of Gastroenterological Surgery, 2008, vol. 41, pages 2075-2080

SUMMARY OF THE INVENTION

Problems to be Solved by the Invention

The present invention aims to provide a uracil detection method comprising a novel uracil-specific reaction, which is capable of detecting uracil highly accurately and economically by a convenient method in a short time. In addition, the present invention provides a reagent for the reaction, and an examination method of DPD deficiency using the reaction.

Means of Solving the Problems

The present inventors have conducted intensive studies in an attempt to solve the aforementioned problems and found that a uracil-specific reaction takes place by using a compound represented by the following formula (I), which resulted in the completion of the present invention.

Accordingly, the present invention relates to the following.
[1] A method of detecting uracil, comprising reacting uracil with a compound represented by the formula (I):

(I)

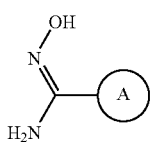

wherein A is an optionally substituted aryl group or an optionally substituted heteroaryl group
(hereinafter sometimes to be abbreviated as compound (I)) to give a fluorescent compound represented by the formula (II):

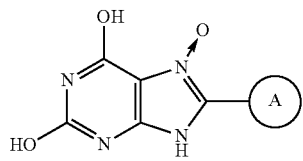

wherein A is as defined above (hereinafter sometimes to be abbreviated as compound (II)).
[2] The method of the above-mentioned [1], wherein A is a substituted aryl group.
[3] The method of the above-mentioned [1], wherein A is a 3-methylphenyl group.
[4] The method of the above-mentioned [3], comprising a step of extracting the fluorescent compound from a sample by using an organic solvent.
[5] The method of the above-mentioned [1], wherein the reaction of uracil and the compound represented by the formula (I) is performed in the presence of an oxidant and a base.
[6] The method of the above-mentioned [5], wherein the oxidant is potassium ferricyanide.
[7] The method of the above-mentioned [5], wherein the amount of the oxidant to be used is 0.001-3 equivalents relative to the compound represented by the formula (I).
[8] The method of the above-mentioned [5], wherein the base is potassium hydroxide.
[9] The method of the above-mentioned [5], wherein the amount of the base to be used is 0.1-2000 equivalents relative to the compound represented by the formula (I).
[10] The method of the above-mentioned [1], wherein the reaction temperature is 50-120° C.
[11] The method of the above-mentioned [1], wherein the reaction time is 1-15 min.
[12] A reagent for uracil detection, comprising a compound represented by the formula (I):

(I)

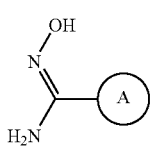

wherein A is as defined for the above-mentioned [1].
[13] The reagent of the above-mentioned [12], wherein A is a substituted aryl group.
[14] The reagent of the above-mentioned [12], wherein A is a 3-methylphenyl group.
[15] A kit for uracil detection, comprising the reagent of the above-mentioned [12].

[16] A fluorescent compound represented by the formula (II):

(II)

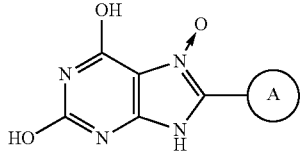

wherein A is as defined for the above-mentioned [1].
[17] The compound of the above-mentioned [16], wherein A is a substituted aryl group.
[18] The compound of the above-mentioned [16], wherein A is a 3-methylphenyl group.
[19] A method of examining dihydropyrimidine dehydrogenase deficiency, comprising detecting uracil in a sample by the method described in the above-mentioned [1].
[20] The method of the above-mentioned [19], wherein the sample is a blood sample and/or a urine sample derived from a human patient.

Effect of the Invention

According to the present invention, uracil can be detected highly accurately and economically by a convenient method in a short time.

BRIEF DESCRIPTION OF THE DRAWINGS

FIG. 6 shows the results of detection of uracil in urine with 3-methylbenzamidoxime.

DESCRIPTION OF EMBODIMENTS

Figure 1:
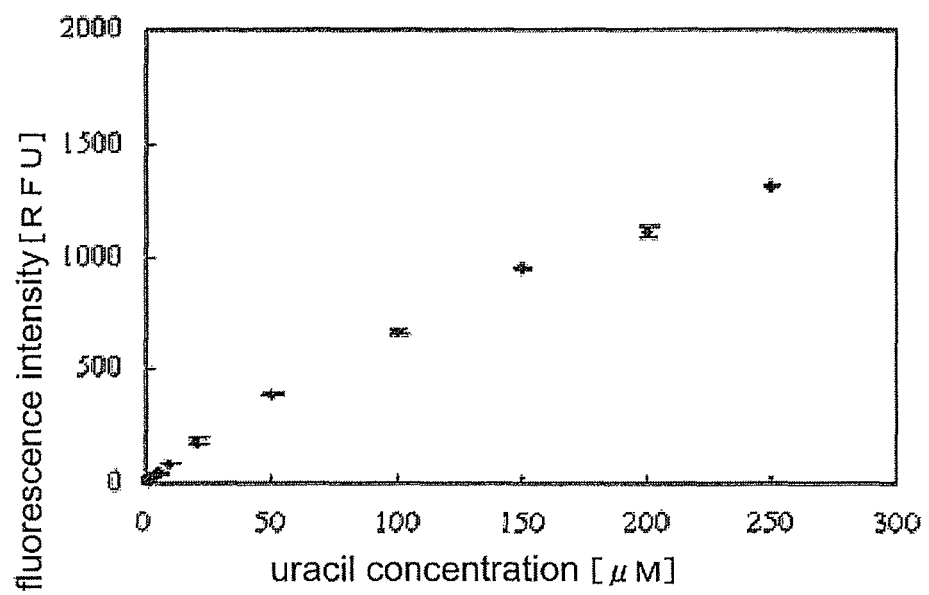
FIG. 1 shows the results of fluorometric analysis of a compound obtained by reacting uracil (each concentration) with 3-methylbenzamidoxime.

The definitions of the terms used in the present invention are described in detail in the following.
The "halogen atom" means a fluorine atom, a chlorine atom, a bromine atom or an iodine atom.
The "alkyl group" is a linear or branched chain alkyl group and, for example, a $C_{1-4}$ alkyl group can be mentioned. Specific examples thereof include methyl, ethyl, n-propyl, isopropyl, n-butyl, isobutyl, sec-butyl, tert-butyl and the like.
The "alkyl group optionally substituted by 1 to 9 halogen atoms" means that wherein the halogen atom is the "halogen atom" defined above and the alkyl moiety thereof is the "alkyl group" defined above. For example, a $C_{1-4}$ alkyl group optionally substituted by 1 to 9 (e.g., 1 to 3) halogen atoms can be mentioned. Specific examples thereof include those recited for the above-mentioned "alkyl group", trifluoromethyl, 2,2,2-trifluoroethyl, pentafluoroethyl and the like.

The "alkenyl group" is a linear or branched chain alkenyl group and, for example, a $C_{1-4}$ alkenyl group can be mentioned. Specific examples thereof include vinyl, allyl, 1-propenyl, isopropenyl, 1-butenyl, 2-butenyl, 3-butenyl, 1-methylallyl, 2-methylallyl, 1-methyl-1-propenyl, 2-methyl-1-propenyl, 1-ethylvinyl and the like.

The "alkynyl group" is a linear or branched chain alkynyl group and, for example, a $C_{1-4}$ alkynyl group can be mentioned. Specific examples thereof include ethynyl, 1-propynyl, 2-propynyl, 1-butynyl, 2-butynyl, 3-butynyl and the like.

The "alkoxy group" is a linear or branched chain alkoxy group and, for example, a $C_{1-4}$ alkoxy group can be mentioned. Examples thereof include methoxy, ethoxy, n-propoxy, isopropoxy, n-butoxy, isobutoxy, sec-butoxy, tert-butoxy and the like.

The "alkoxy group optionally substituted by 1 to 9 halogen atoms" means that wherein the halogen atom is the "halogen atom" defined above and the alkoxy moiety thereof is the "alkoxy group" defined above. For example, a $C_{1-4}$ alkoxy group optionally substituted 1 to 9 (e.g., 1 to 5) halogen atoms can be mentioned. Specific examples thereof include those recited for the above-mentioned "alkoxy group", trifluoromethoxy, 2,2,2-trifluoroethoxy, pentafluoroethoxy and the like.

Examples of the "aryl group" of the "optionally substituted aryl group" include a $C_{6-10}$ aryl group. Specific examples thereof include phenyl, naphthyl and the like, and particularly preferred is phenyl.

As the "substituent" of the "optionally substituted aryl group", the substituent selected from the substituent group below (hereinafter to be abbreviated as substituent group A) can be mentioned. The aryl group may be substituted by 1 to 3 substituents at substitutable position(s). When two or more substituents are present, the respective substituents may be the same or different.

Substituent Group A:
(1) alkyl group optionally substituted by 1 to 9 halogen atoms,
(2) alkenyl group,
(3) alkynyl group, and
(4) alkoxy group optionally substituted by 1 to 9 halogen atoms.

As the "heteroaryl group" of the "optionally substituted heteroaryl group", the following can be mentioned:
a monocyclic $C_{5-6}$ heteroaryl group having, besides carbon atom, 1-4 hetero atoms selected from nitrogen atom, oxygen atom and sulfur atom;
a fused cyclic $C_{9-13}$ heteroaryl group wherein a monocyclic $C_{5-6}$ heteroaryl group having, besides carbon atom, 1-4 hetero atoms selected from nitrogen atom, oxygen atom and sulfur atom and a $C_{6-10}$ aryl group are fused; and
a fused cyclic $C_{8-10}$ heteroaryl group wherein monocyclic $C_{5-6}$ heteroaryl groups having, besides carbon atom, 1-4 hetero atoms selected from nitrogen atom, oxygen atom and sulfur atom are fused. Specifically, pyridyl, pyrazyl, pyrimidyl, pyridazyl, triazinyl, pyrrolyl, imidazolyl, pyrazolyl, triazolyl, tetrazolyl, furyl, oxazolyl, thienyl, thiazolyl, quinolinyl, quinoxalinyl, quinazolinyl, cinnolinyl, indolyl, benzimidazolyl, benzotriazolyl, benzofuryl, benzothienyl, benzoxazolyl, benzothiazolyl and the like can be mentioned.

As the "substituent" of the "optionally substituted heteroaryl group", the substituent selected from the above-mentioned substituent group A can be mentioned. The heteroaryl group may be substituted by 1 to 3 substituents at substitutable position(s). When two or more substituents are present, the respective substituents may be the same or different.

A preferable embodiment of the present invention is explained below.

The present invention provides a detection method of uracil, which comprises reacting uracil with a compound represented by the formula (I) to give a fluorescent compound represented by the formula (II).

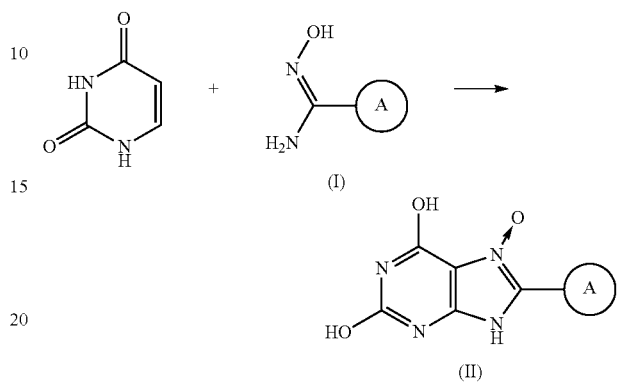

In the above-mentioned formula (I) and the formula (II), A is an optionally substituted aryl group or an optionally substituted heteroaryl group.

Preferred as A is an optionally substituted aryl group, more preferred is a $C_{6-10}$ aryl group optionally substituted by 1 to 3 substituents selected from the above-mentioned substituent group A. Particularly preferred is a $C_{6-10}$ aryl group substituted by 1 to 3 alkyl (e.g., $C_{1-4}$ alkyl) groups optionally substituted by 1 to 9 (e.g., 1 to 3) halogen atoms, more preferred is 3-methylphenyl or 4-trifluoromethylphenyl, and particularly preferred is 3-methylphenyl.

Since uracil can be detected with high sensitivity, A is also preferably unsubstituted phenyl.

As compound (I), the following compounds (I-A)-(I-E) are preferable.

[Compound (I-A)]
Compound (I) wherein A is an optionally substituted aryl group.

[Compound (I-B)]
Compound (I) wherein A is a $C_{6-10}$ aryl group optionally substituted by 1 to 3 substituents selected from the above-mentioned substituent group A.

[Compound (I-C)]
Compound (I) wherein A is a $C_{6-10}$ aryl group substituted by 1 to 3 alkyl (e.g., alkyl) groups optionally substituted by 1 to 9 (e.g., 1 to 3) halogen atoms.

[Compound (I-D)]
Compound (I) wherein A is 3-methylphenyl, phenyl or 4-trifluoromethylphenyl.

[Compound (I-E)]
A compound represented by the formula:

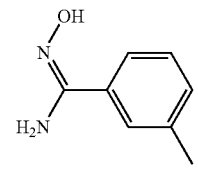

(namely, 3-methylbenzamidoxime).

Compound (I) is commercially available or can be produced by a method known per se.

As compound (II), the following compounds (II-A)-(II-E) are preferable.

[Compound (II-A)]

Compound (II) wherein A is an optionally substituted aryl group.

[Compound (II-B)]

Compound (II) wherein A is a $C_{6-10}$ aryl group optionally substituted by 1 to 3 substituents selected from the above-mentioned substituent group A.

[Compound (II-C)]

Compound (II) wherein A is a $C_{6-10}$ aryl group optionally substituted by 1 to 3 alkyl (e.g., $C_{1-4}$ alkyl) groups optionally substituted by 1 to 9 (e.g., 1 to 3) halogen atoms.

[Compound (II-D)]

Compound (II) wherein A is 3-methylphenyl, phenyl or 4-trifluoromethylphenyl.

[Compound (II-E)]

A fluorescent compound represented by the formula:

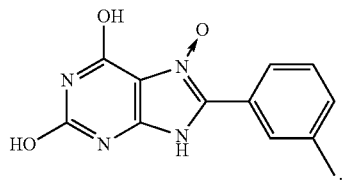

A fluorescent compound wherein, like compound (II-E), a hydrophobic functional group such as an alkyl group (preferably a methyl group) and the like is introduced into a phenyl group is particularly preferable since it can be extracted with an organic solvent (e.g., ethyl acetate). Since extraction from the urine or blood with an organic solvent is possible, multiple samples can be measured in a short time without being influenced by a fluorescent impurity in a sample (urine, blood).

Since the above-mentioned reaction of uracil with compound (I) (hereinafter to be also referred to as the reaction in the present invention) preferably proceeds in the presence of an oxidant and a base (particularly, strong base), further addition of an oxidant and a base is preferable.

As the oxidant, an oxidant known per se can be appropriately used. Examples of the oxidant include potassium ferricyanide, ferric chloride, cupric chloride, sodium iodate, potassium permanganate, potassium nitrate, ceric ammonium nitrate, potassium dichromate and the like. Particularly preferred is potassium ferricyanide. The amount of the oxidant to be used is, for example, 0.001-3 equivalents, preferably 0.5-2.5 equivalents, relative to compound (I).

As the base, a base known per se can be appropriately used. Examples of the base include potassium hydroxide, sodium hydroxide, lithium hydroxide, magnesium hydroxide, calcium hydroxide, potassium carbonate, sodium carbonate, lithium carbonate, potassium hydrogencarbonate, sodium hydrogencarbonate, lithium hydrogencarbonate and the like. Particularly preferred is potassium hydroxide. The amount of the base to be used is, for example, 0.1-2000 equivalents, preferably 100-1000 equivalents, relative to compound (I).

Since the reaction preferably proceeds by heating, the reaction in the present invention is preferably performed at a reaction temperature of 50-120° C., more preferably 80-120° C., particularly preferably 90° C.

Since the fluorescence intensity of compound (II) obtained by a reaction in an extremely short time or a reaction in a long time decreases, the reaction in the present invention is preferably performed in a reaction time of 1-15 min, more preferably 1-5 min, particularly preferably 2 min.

The reaction in the present invention can also be performed using a solvent. The solvent is not particularly limited as long as the reaction proceeds, and a solvent known per se can be used. Examples thereof include water, N,N-dimethylformamide, dimethyl sulfoxide, alcohols (e.g., methanol, ethanol, 1-propanol, 2-propanol, 1-butanol, 2-butanol, isobutanol, sec-butanol, tert-butanol etc.) and the like. Particularly preferred is water. In addition, water contained in the following sample may also function as a solvent.

Since compound (II) obtained by the reaction in the present invention is fluorescent, uracil can be detected by irradiating an excitation light in the excitation wavelength range to compound (II), and measuring the fluorescence intensity in the fluorescence wavelength range.

The excitation wavelength range is not particularly limited as long as compound (II) shows fluorescence by irradiating an excitation light, and those of ordinary skill in the art can properly select an appropriate wavelength range and perform the measurement. For example, irradiation of an excitation light in a 250-400 nm wavelength range is preferable, that in a 310-350 nm wavelength range is more preferable, and that at a 310-330 nm wavelength is particularly preferable.

The fluorescence wavelength range is not particularly limited as long as it is a fluorescence wavelength range, and those of ordinary skill in the art can properly select an appropriate wavelength range and perform the measurement. For example, measurement of fluorescence intensity in a 350-500 nm wavelength range is preferable, that in a 360-440 nm wavelength range is more preferable, and that at a 365-410 nm wavelength is particularly preferable.

The fluorescence intensity can be measured by a detection method known per se, and can be measured using, for example, a fluorescence spectrophotometer.

A reaction mixture containing compound (II) obtained by the reaction in the present invention is strong alkaline immediately after reaction. A treatment such as neutralization with an acid (e.g., acetic acid), salting out with a salt (e.g., sodium chloride), extraction with an organic solvent (e.g., ethyl acetate) and the like is preferably further performed to enhance fluorescence intensity.

Neutralization (pH 6-7) step→salting out step→extraction step is particularly preferably performed.

Compound (I) can be used as a reagent for uracil detection singly or together with other additives. Examples of the additive include an acid, an acidic reagent and the like.

As the "acid", an inorganic acid or organic acid can be mentioned. Examples thereof include hydrochloric acid, sulfuric acid, nitric acid, acetic acid, formic acid and the like.

As the "acidic reagent", an aqueous solution of the acid and the like can be mentioned.

A reagent for uracil detection can be used in a uracil detection kit singly or together with other items. Examples of the item include an oxidant, a base and a solvent, instructions, a packaging material, a reaction container, a pre-treatment filter for body fluid sample or waste product sample, and the like, which can aid advantageous progress of the reaction in the present invention.

As the oxidant, base and solvent, those similar to the examples recited above can be mentioned.

The instructions may describe a detection target, a sample to be used, a use method and a storage method (e.g., chilled storage, preservation in closed container etc.) and the like.

As the packaging material, reaction container and pre-treatment filter for body fluid sample or waste product sample, those known per se can be used.

The reaction in the present invention is specific to uracil. Being "specific to uracil" means reaction with uracil alone and no reaction with, for example, nucleic acid base, nucleoside, nucleotide and nucleic acid base derivatives (e.g., rare nucleic acid base such as pseudouridine and the like, fluorinated pyrimidine anti-cancer agent such as 5-fluorouracil and the like, etc.) and the like other than free uracil.

Since such reaction in the present invention is specific to uracil, dihydropyrimidine dehydrogenase deficiency can be examined by detecting uracil in a sample using the reaction in the present invention.

As the sample, for example, body fluid samples (e.g., blood sample etc.) and/or waste product samples (e.g., urine sample etc.) derived from mammals (e.g., human (particularly human patients) etc.) can be mentioned.

In addition, since the reaction in the present invention is specific to uracil, it is also useful for cell staining, sequencing of the base sequence of RNA and the like.

EXAMPLES

The present invention is explained in more detail in the following by referring to Examples, Reference Examples and Experimental Examples, which are not to be construed as limitative.

Example 1

Reaction of Uracil with 3-methylbenzamidoxime

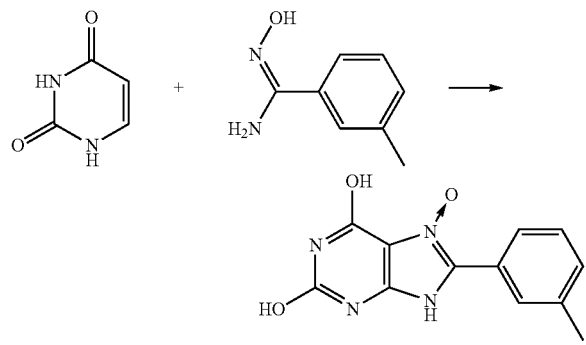

Aqueous uracil solution (0 μm (Reference Example), 1 μM, 2 μM, 5 μM, 10 μm, 20 μm, 50 μm, 100 μm, 150 μm, 200 μm or 250 μm, each 0.25 ml), aqueous 3-methylbenzamidoxime solution (4 mM, 0.25 ml), aqueous potassium ferricyanide solution (8 mM, 0.25 ml) and aqueous potassium hydroxide solution (4 M, 0.25 ml) were mixed, and the mixture was heated at 90° C. for 2 min. The obtained compound was subjected to fluorometric analysis under the following conditions. The measurement results of fluorometric analysis are shown in Table 1, FIG. 1, FIG. 2.

Fluorometric Analysis:
Type of equipment: JASCO FP-6300 Spectrofluorometer
Ex/Em=330 nm/410 nm
Slit width: 5 nm, 5 nm
Sensitivity: medium
Response: medium

TABLE 1

Table 1. uracil concentration and fluorescence intensity of obtained compounds

| uracil concentration (μM) | fluorescence intensity (RFU) |
|---|---|
| 0 (Reference Example) | 0.2 |
| 1 | 9.8 |
| 2 | 17.5 |
| 5 | 42.0 |
| 10 | 86.0 |
| 20 | 179 |
| 50 | 391 |
| 100 | 668 |
| 150 | 950 |
| 200 | 1113 |
| 250 | 1310 |

Example 2

Reaction of Uracil with 4-trifluoromethylbenzamidoxime

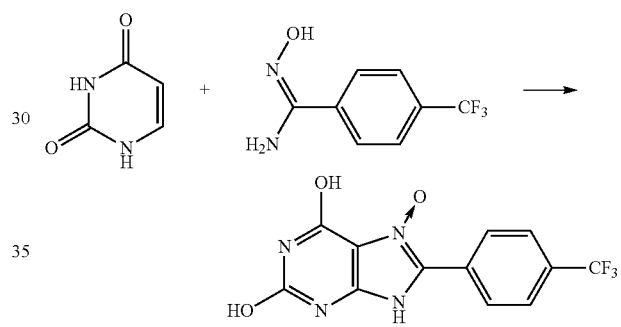

Figure 3:
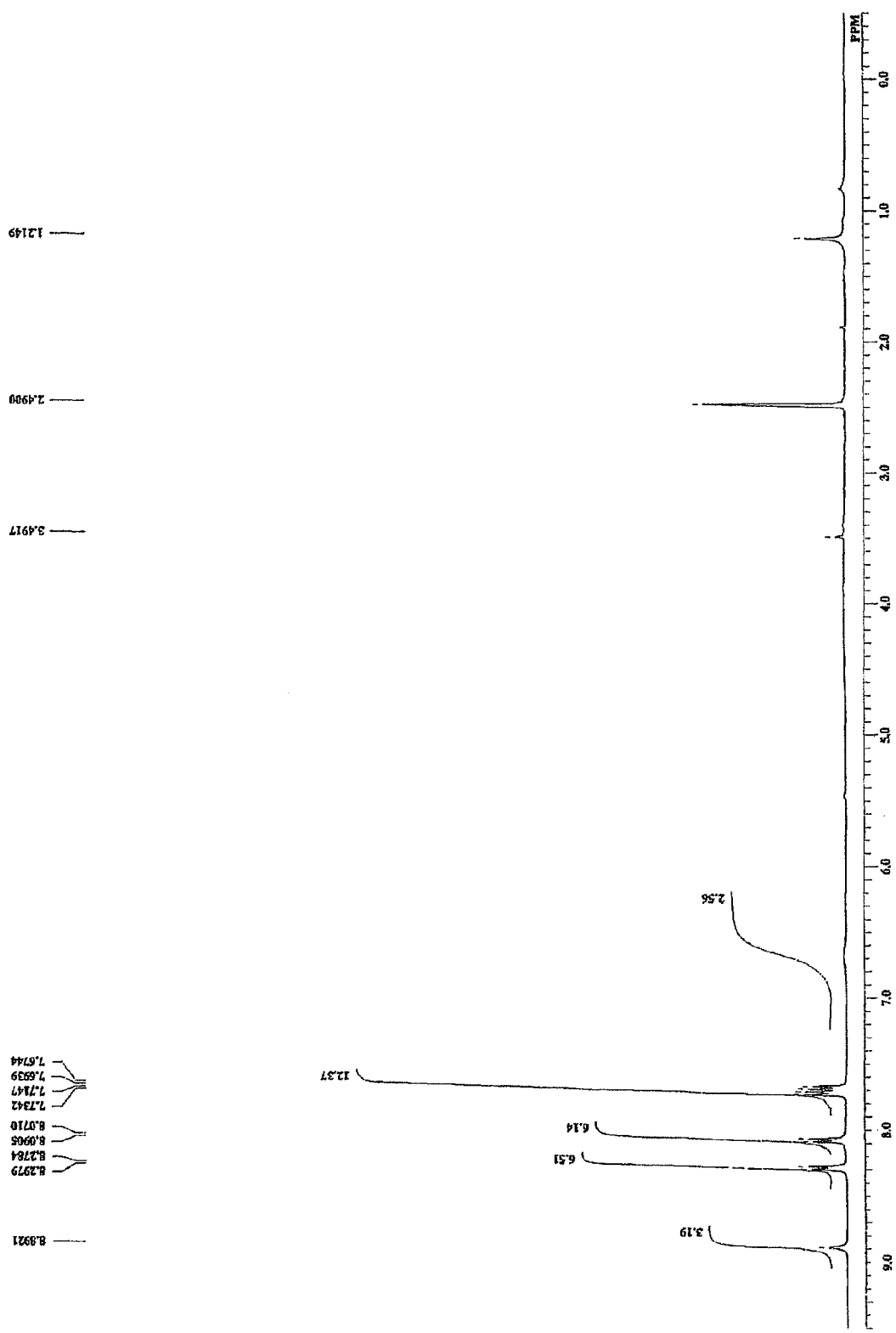
FIG. 3 shows the $^1$H-NMR spectrum of a compound obtained by reacting uracil with 4-trifluoromethylbenzamidoxime.

Aqueous uracil solution (1 mM, 100 ml), 4-trifluoromethylbenzamidoxime (4 mM, 100 ml), aqueous potassium ferricyanide solution (8.0 mM, 100 ml) and aqueous potassium hydroxide solution (2 M, 100 ml) were mixed, and the mixture was heated at 100° C. for 10 min. After the reaction, the reaction mixture was extracted with ethyl acetate, and the obtained organic layer was concentrated. This operation was repeated 13 times, and the obtained residues were mixed and purified by silica gel column chromatography (eluent: ethyl acetate/methanol=9/1→8/2→7/3) to give the object compound (25 mg) as a white powder (yield: 6%). The obtained compound was subjected to $^1$H-NMR. The results are shown in FIG. 3. Measuring machine: varian UNITY plus 500 (500 MHz)

$^1$H NMR (DMSO-$d_6$, 400 MHz) δ=8.89 (broad s, 0.25H), 8.29 (d, J=8.0 Hz, 0.5H), 8.08 (d, J=7.8 Hz, 0.5H), 7.72 (d, J=8.0 Hz, 0.5H), 7.68 (d, J=7.8 Hz, 0.5H), 6.68 (broad s, 0.25H).

Figure 2:
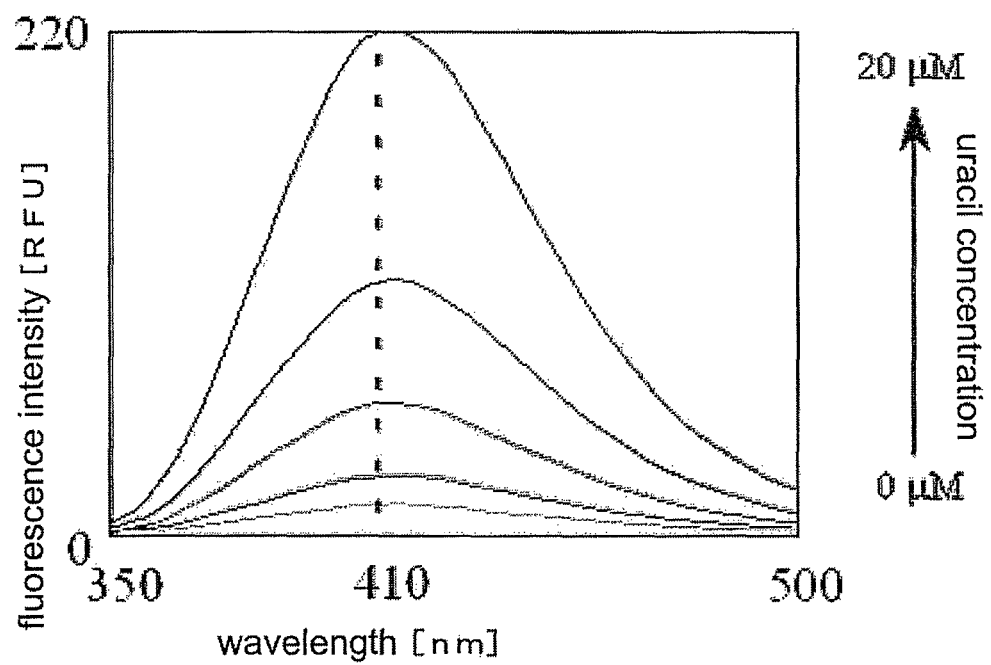
FIG. 2 shows the results of fluorometric analysis of a compound obtained by reacting uracil (each concentration) with 3-methylbenzamidoxime.

From the above, it has been found that the reaction of uracil and compound (I) produces compound (II) (FIG. 3), and compound (II) is a fluorescent compound (Table 1, FIG. 1). In addition, it has been found that the uracil concentration and the fluorescence intensity are correlated (Table 1, FIG. 1). Furthermore, it has been found that the fluorescence intensity becomes the highest at a 410 nm fluorescence wavelength (FIG. 2).

Reference Example 1

Reaction of Sample Other than Uracil with 3-methylbenzamidoxime

Figure 4:
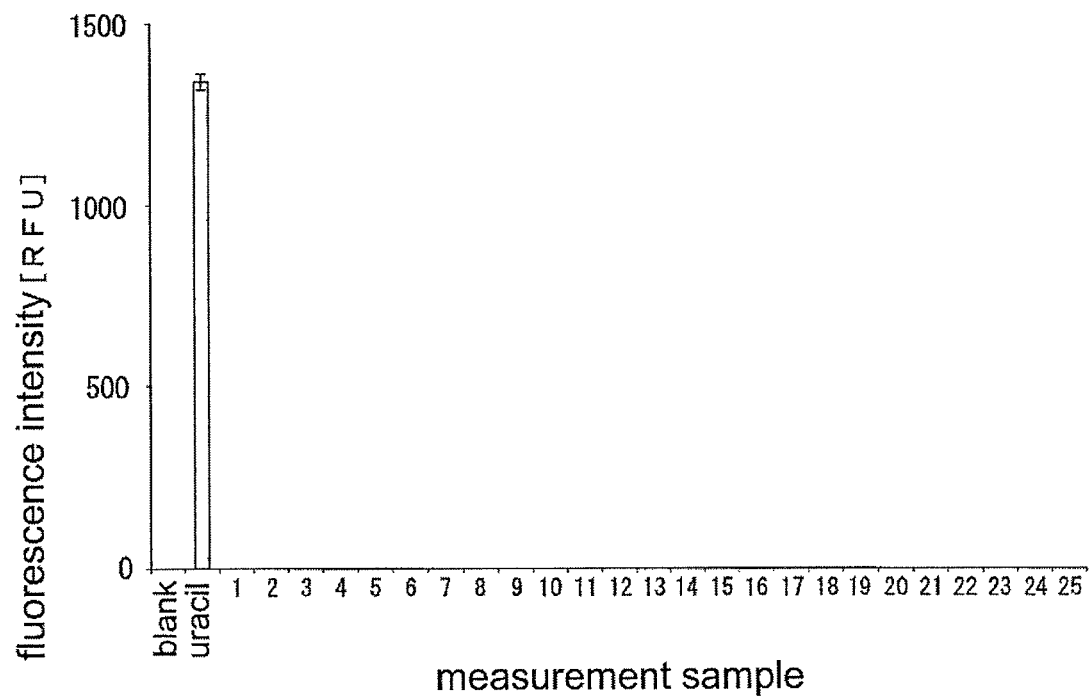
FIG. 4 shows the results of fluorometric analysis of a compound obtained by reacting a sample other than uracil with 3-methylbenzamidoxime.

In the same manner as in Example 1 except that uracil was changed to the measurement samples shown in the following Table 2, fluorometric analysis was performed. The results are shown in FIG. 4.

TABLE 2

Table 2. Measurement sample

| sample No. | | measurement sample |
|---|---|---|
| 1 | nucleic | cytosine |
| 2 | acid base | thymine |
| 3 | | adenine |
| 4 | | guanine |
| 5 | nucleoside | uridine |
| 6 | | cytidine |
| 7 | | thymidine |
| 8 | | adenosine |
| 9 | | guanosine |
| 10 | nucleotide | 5'-UMP |
| 11 | | 5'-CMP |
| 12 | | 5'-dTMP |
| 13 | | 5'-AMP |
| 14 | | 5'-GMP |
| 15 | nucleic | pseudouridine |
| 16 | acid base | 5-fluorouracil |
| 17 | derivative | 1-methyluracil |
| 18 | | 6-methyluracil |
| 19 | | 5,6-dihydrouracil |
| 20 | saccharide | glucose |
| 21 | | fructose |
| 22 | | lactose |
| 23 | | ribose |
| 24 | | sucrose |
| 25 | amino acids | mixture of amino acids (20 kinds) constituting living organisms |

From the above, it has been found that the reaction in the present invention has very high substrate specificity, and does not provide fluorescence to nucleic acid base, nucleoside, nucleotide, nucleic acid base derivative (e.g., rare nucleic acid base such as pseudouridine and the like, fluorinated pyrimidine anti-cancer agent such as 5-fluorouracil and the like, uracil metabolite such as dihydrouracil and the like, methyluracil etc.) and the like, other than free uracil (FIG. 4).

Example 3

Quantification of Urinal Uracil Concentration (Direct Quantification of Urinal Uracil)

(Reagent: Total 1 mL)
Reagent Composition A (Test Reagent)
(1) 8% diluted urine (urine sample: healthy volunteer (37-year-old, male)): 125 μL
(2) Water or uracil standard solution: 125 μL
(3) 4 mM aqueous 3-methylbenzamidoxime solution: 250 μL
(4) 8 mM aqueous potassium ferricyanide solution: 250 μL
(5) 2 M aqueous potassium hydroxide solution: 250 μL
Reagent Composition B (Fluorescent Blank Derived from Urine)
(1) 8% diluted urine (urine sample: healthy individual volunteer (37-year-old, male)): 125 μL
(2) Water: 125 μL
(3) Water: 250 μL
(4) 8 mM aqueous potassium ferricyanide solution: 250 μL
(5) 2 M aqueous potassium hydroxide solution: 250 μL
Reagent Composition C (Fluorescent Blank Derived from Reagent)
(1) Water: 125 μL,
(2) Water: 125 μL
(3) 4 mM aqueous 3-methylbenzamidoxime solution: 250 μL
(4) 8 mM aqueous potassium ferricyanide solution: 250 μL
(5) 2 M aqueous potassium hydroxide solution: 250 μL
(Operation)
(1) The reagents with the above-mentioned compositions were sequentially added to reaction containers
(2) The mixture was heated at 90° C. for 2 min and
(3) Cooled in ice bath for 2 min
(4) The fluorescence intensity of the reaction mixture was measured (measurement conditions followed those in Example 1)
(5) Creatinine concentration of the same urine was measured The creatinine concentration was measured by either of the following two kinds of methods. Both methods were performed according to the attached instructions for the detail of the steps.
Method 1

In this method, AUTION sticks 10PA (ARKRAY Factory, Shiga, Japan), which is urine test paper, was used.
(Operation)
(1) Test paper was immersed in urine for 2 seconds
(2) Excess urine on the test paper was gently wiped, and the test paper was horizontally maintained and stood for 60 seconds
(3) Creatinine concentration was determined based on the color change of the test paper
Method 2

In this method, Creatinine Assay Kit (Cayman, Mich., USA) was used.
(Operation)
(1) Alkaline Picrate Solution (150 μL) attached to the kit was added to 15 μL of 10-fold diluted urine, and the mixture was incubated at room temperature for 10 min.
(2) The absorbance at 490-500 nm was measured (Initial absorbance: $I_{abs}$)
(3) Acid Solution (5 μL) attached to the kit was added to the solution, and the mixture was incubated at room temperature for 20 min.
(4) The absorbance at 490-500 nm was measured (Final absorbance: $F_{abs}$)
(5) Using the analytical curve prepared using a creatinine standard solution, the creatinine concentration was calculated from $F_{abs}-I_{abs}$ values.
(Results)

The fluorescence intensity derived from urinal uracil produced by a fluorescent derivatization reaction is obtained by subtracting each value of fluorescence intensity obtained with reagent composition B and reagent composition C from the intensity obtained by the reaction with reagent composition A, and an addition analytical curve is drawn, from which urinal uracil concentration can be quantified. By creatinine correction of the value obtained from the analytical curve, the value of 14.1 μmol/g Cre was obtained. This value is within the range of average urinal uracil concentration of Japanese people. The creatine correction was performed to avoid a urine volume error of urinal uracil. From the above results, it has been clarified that the method of the present invention can quantify urinal uracil.

Experimental Example 1

Figure 5:
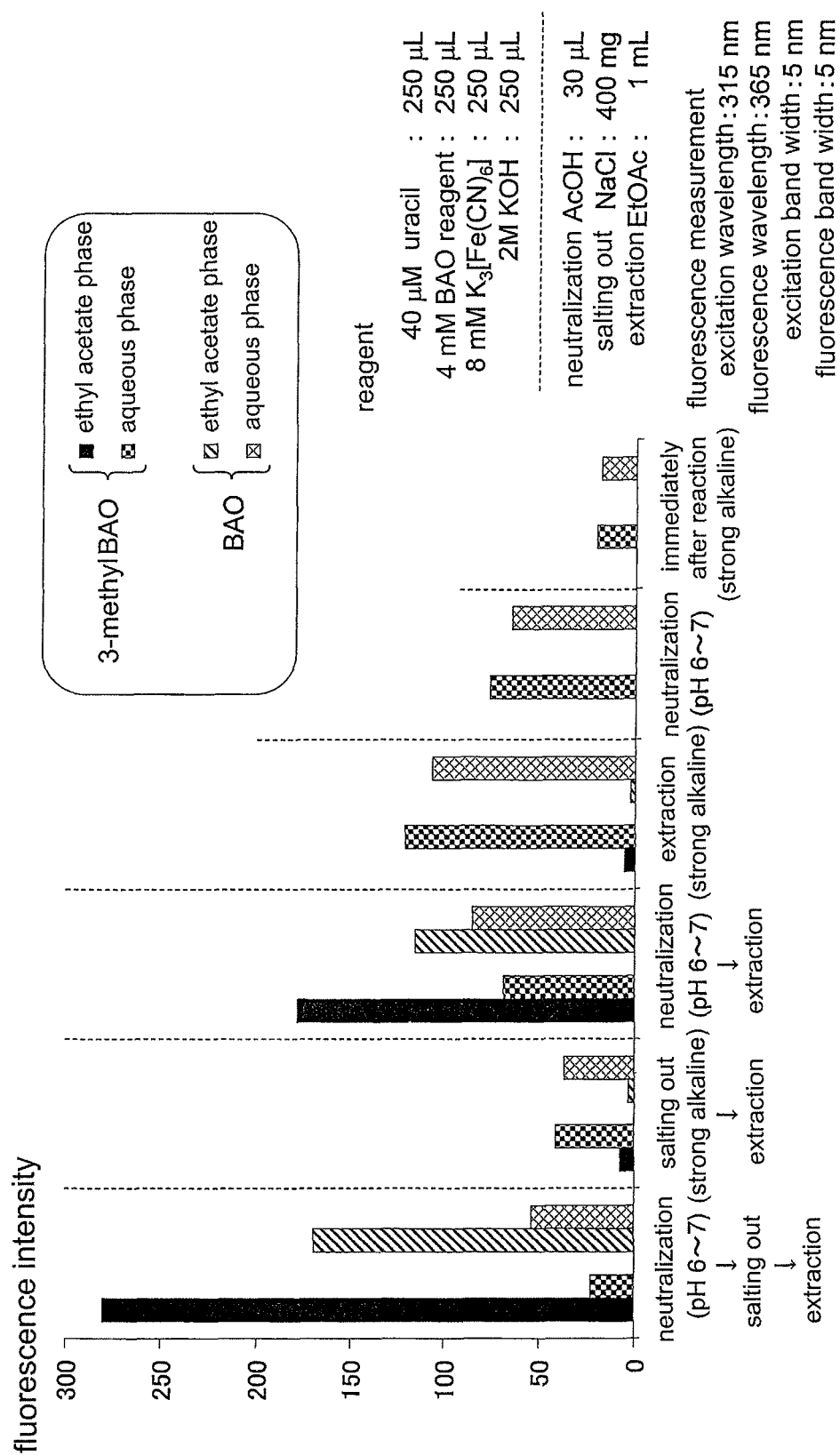
FIG. 5 shows the results of fluorometric analysis of a compound obtained by reacting uracil with 3-methylbenzamidoxime, or uracil with benzamidoxime, and treated under various conditions.

Extraction of Compound (II) (Fluorescent Compound) with Organic Solvent (i) Aqueous uracil solution (40 μm, 0.25 ml), (ii) compound (I) [aqueous 3-methylbenzamidoxime solution or aqueous benzamidoxime solution] (4 mM, 0.25 ml), (iii) aqueous potassium ferricyanide solution (8 mM, 0.25 ml) and aqueous potassium hydroxide solution (2 M, 0.25 ml) were mixed, and the mixture was heated at 90° C. for 2 min. The reaction mixture was treated under the conditions shown in FIG. 5, and fluorometric analysis was further performed under the following conditions. The measurement results of fluorometric analysis are shown in FIG. 5.

Fluorometric Analysis:
Type of equipment: JASCO FP-6300 Spectrofluorometer
Ex/Em=315 nm/365 nm
Excitation band width: 5 nm
Fluorescence band width: 5 nm When 3-methylbenzamidoxime was used as compound (I), a remarkable increase in the fluorescence intensity was observed by extraction with an organic solvent after neutralization.

Example 4

Quantification of Urinal Uracil Concentration (Quantification of Urinal Uracil Via Solvent Extraction)

(Reagent: Total 1 mL)
(1) 8% diluted urine (urine sample: healthy individual volunteer (23-year-old, male)): 125 μL
(2) Water or uracil standard solution: 125 μL
(3) 4 mM aqueous 3-methylbenzamidoxime solution: 250 μL
(4) 8 mM aqueous potassium ferricyanide solution: 250 μL
(5) 2 M aqueous potassium hydroxide solution: 250 μL
(Operation)
(1 The reagents with the above-mentioned compositions were sequentially added to reaction containers
(2) The mixture was heated at 90° C. for 2 min and
(3) Cooled in ice bath for 2 min
(4) Acetic acid (30 μL) was added and blended
(5) Sodium chloride (400 mg) was added and the mixture was vigorously blended
(6) Ethyl acetate (1 mL) was added and the mixture was vigorously blended
(7) The fluorescence intensity of the upper layer was measured (measurement conditions followed those in Example 1)
(8) Creatinine concentration of the same urine was measured (measurement conditions followed those in Example 3)
(Results)

The results are shown in FIG. 6. By creatinine correction of the value obtained from the analytical curve, the value of 40.1 μmol/g Cre was obtained. This value is within the range of average urinal uracil concentration of Japanese people. The creatine correction was performed to avoid a urine volume error of urinal uracil.

From the above results, it has been clarified that, when urine contains a large amount of fluorescent impurity substances, the method of the present invention can properly quantify urinal uracil by extraction with an organic solvent.

INDUSTRIAL APPLICABILITY

Since the reaction in the present invention is specific to uracil, uracil can be detected highly accurately and economically by a convenient method in a short time by using the reaction in the present invention. In addition, since the uracil concentration and the fluorescence intensity of the compound obtained by the reaction in the present invention are correlated, uracil can be quantified by the reaction in the present invention, without using a special technique. Therefore, using the method of the present invention, DPD deficiency can be conveniently examined, which is advantageous for the chemical therapy of cancer.

This application is based on patent application No. 2010-44610 filed in Japan, the contents of which are incorporated in full herein.

The invention claimed is:

1. A method of detecting uracil, comprising reacting uracil with a compound represented by the formula (I):

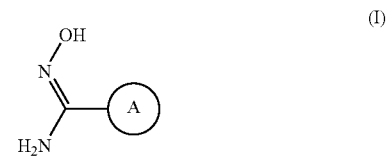

wherein A is a $C_{6-10}$ aryl group substituted by a $C_{1-4}$ alkyl group,
in the presence of an oxidant and a base, wherein the base is present in an amount of 100-1000 equivalents relative to the compound represented by the formula (I),
to give a fluorescent compound represented by the formula (II):

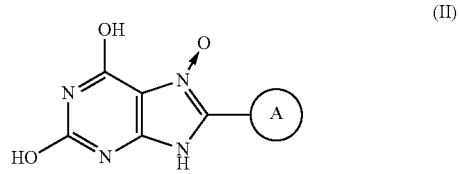

wherein A is as defined above.

2. The method according to claim 1, wherein A is a 3-methylphenyl group.

3. The method according to claim 2, comprising a step of extracting the fluorescent compound from a sample by using an organic solvent.

4. The method according to claim 1, wherein (i) the oxidant is potassium ferricyanide and/or (ii) the base is potassium hydroxide.

5. The method according to claim 1, wherein the oxidant is present in an amount of 0.001-3 equivalents relative to the compound represented by the formula (I).

6. The method according to claim 1, wherein (i) the reaction temperature is 50-120° C. and/or (ii) the reaction time is 1-15 minutes.

7. A reagent for uracil detection, comprising a compound represented by the formula (I):

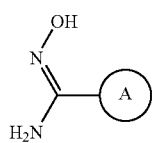 (I)

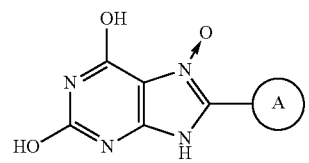 (II)

wherein A is a $C_{6-10}$ aryl group substituted by a $C_{1-4}$ alkyl group.

8. The reagent according to claim 7, wherein A is a 3-methylphenyl group.

9. A kit for uracil detection, comprising the reagent of claim 7.

10. A fluorescent compound represented by the formula (II):

wherein A is a $C_{6-10}$ aryl group substituted by a $C_{1-4}$ alkyl group.

11. The compound according to claim 10, wherein A is a 3-methylphenyl group.

12. A method of examining dihydropyrimidine dehydrogenase deficiency, comprising detecting uracil in a blood sample and/or a urine sample derived from a human patient, by the method according to claim 1.

\* \* \* \* \*

UNITED STATES PATENT AND TRADEMARK OFFICE
CERTIFICATE OF CORRECTION

PATENT NO. : 8,871,520 B2  
APPLICATION NO. : 13/582356  
DATED : October 28, 2014  
INVENTOR(S) : Kai et al.

Page 1 of 1

It is certified that error appears in the above-identified patent and that said Letters Patent is hereby corrected as shown below:

On the Title Page

Item "(73) Assignee: Nagasaki University, Kagasaki (JP)"

should read

Item "(73) Assignee: Nagasaki University, Nagasaki (JP)"

Signed and Sealed this
Sixteenth Day of June, 2015

Michelle K. Lee
*Director of the United States Patent and Trademark Office*